(12) United States Patent
Ribble et al.

(10) Patent No.: US 10,037,674 B2
(45) Date of Patent: Jul. 31, 2018

(54) EQUIPMENT, DRESSING, AND GARMENT WIRELESS CONNECTIVITY TO A PATIENT BED

(71) Applicant: Hill-Rom Services, Inc., Batesville, IN (US)

(72) Inventors: David L. Ribble, Indianapolis, IN (US); David C. Newkirk, Lawrenceburg, IN (US); Michael S. Hood, Batesville, IN (US); Joshua P. Lingenfelser, Fuquay Varina, NC (US); Robert M. Zerhusen, Cincinnati, OH (US); Steven A. Dixon, Riverview, FL (US); Timothy D. Wildman, Metamora, IN (US)

(73) Assignee: Hill-Rom Services, Inc., Batesville, IN (US)

( * ) Notice: Subject to any disclaimer, the term of this patent is extended or adjusted under 35 U.S.C. 154(b) by 0 days.

(21) Appl. No.: 15/617,514

(22) Filed: Jun. 8, 2017

(65) Prior Publication Data
US 2017/0270766 A1    Sep. 21, 2017

Related U.S. Application Data

(63) Continuation of application No. 14/879,179, filed on Oct. 9, 2015, now Pat. No. 9,711,029.
(Continued)

(51) Int. Cl.
*G08B 23/00*    (2006.01)
*G08B 21/04*    (2006.01)
(Continued)

(52) U.S. Cl.
CPC ........ *G08B 21/0461* (2013.01); *A61B 5/1115* (2013.01); *A61B 5/1117* (2013.01);
(Continued)

(58) Field of Classification Search
CPC ............ A61G 2205/20; A61G 2205/60; A61G 7/0507; A61G 7/05776; G08B 21/0461;
(Continued)

(56) References Cited

U.S. PATENT DOCUMENTS

| 5,010,772 A | 4/1991 | Bourland et al. |
| 5,253,656 A | 10/1993 | Rincoe et al. |

(Continued)

FOREIGN PATENT DOCUMENTS

| EP | 2 767 918 | 8/2014 |
| GB | 2492028 A | 12/2012 |
| WO | WO 2015/137999 A1 | 9/2015 |

OTHER PUBLICATIONS

Ford, Steve, *Trust introduces red socks to identify falls risk patients*, Nursing Times, May 10, 2013 (3 pages).
(Continued)

*Primary Examiner* — Naomi J Small
(74) *Attorney, Agent, or Firm* — Barnes & Thornburg LLP (57) ABSTRACT

A system comprises a patient bed having a reader to read wireless signals. In some embodiments a wound dressing has a transmitter that transmits wireless signals to the reader of the patient bed. In other embodiments, a garment has a transmitter that transmits wireless signals to the reader of the patient bed. In still further embodiments, other medical equipment has a transmitter that transmits wireless signals to the reader of the patient bed.

18 Claims, 5 Drawing Sheets

Related U.S. Application Data (60) Provisional application No. 62/073,098, filed on Oct. 31, 2014.

(51) Int. Cl.
*A61G 7/05* (2006.01)
*A61G 7/057* (2006.01)
*A61B 5/11* (2006.01)
*A61B 5/00* (2006.01)

(52) U.S. Cl.
CPC ....... *A61G 7/0507* (2013.01); *A61G 7/05776* (2013.01); *A61B 5/0024* (2013.01); *A61B 5/6807* (2013.01); *A61G 2205/20* (2013.01); *A61G 2205/60* (2013.01)

(58) Field of Classification Search
CPC ... A61B 5/0024; A61B 5/1115; A61B 5/1117; A61B 5/6807
USPC ...................................................... 340/573.4
See application file for complete search history.

(56) References Cited

U.S. PATENT DOCUMENTS

| | | | |
|---|---|---|---|
| 5,276,432 A * | 1/1994 | Travis ................... | A61B 5/1115 177/144 |
| 6,073,291 A * | 6/2000 | Davis ................... | A61B 6/0485 414/676 |
| 6,208,250 B1 | 3/2001 | Dixon et al. | |
| 6,438,776 B2 | 8/2002 | Ferrand et al. | |
| 6,585,328 B1 | 7/2003 | Oexman et al. | |
| 6,924,441 B1 | 8/2005 | Mobley et al. | |
| 7,113,081 B1 | 9/2006 | Reichow et al. | |
| 7,154,397 B2 | 12/2006 | Zerhusen et al. | |
| 7,253,366 B2 | 8/2007 | Bhai | |
| 7,319,386 B2 | 1/2008 | Collins, Jr. et al. | |
| 7,409,735 B2 | 8/2008 | Kramer et al. | |
| 7,679,520 B2 | 3/2010 | Zerhusen et al. | |
| 7,911,349 B2 | 3/2011 | Zerhusen et al. | |
| 8,272,276 B2 | 9/2012 | Gorjanc et al. | |
| 8,368,545 B2 | 2/2013 | Zerhusen et al. | |
| 8,404,921 B2 | 3/2013 | Lee et al. | |
| 8,674,839 B2 | 3/2014 | Zerhusen et al. | |
| 8,691,266 B2 | 4/2014 | Gladman et al. | |
| 8,736,439 B1 * | 5/2014 | Shinozuka ............ | G08B 21/22 340/539.11 |
| 9,711,029 B2 | 7/2017 | Ribble et al. | |
| 2006/0049936 A1 | 3/2006 | Collins, Jr. | |
| 2007/0159332 A1 * | 7/2007 | Koblasz ................ | A61B 5/1117 340/572.1 |
| 2007/0210917 A1 * | 9/2007 | Collins, Jr. .......... | A61B 5/1117 340/539.1 |
| 2009/0044334 A1 | 2/2009 | Parsell et al. | |
| 2009/0049610 A1 | 2/2009 | Heimbrock et al. | |
| 2009/0049936 A1 | 2/2009 | Mian et al. | |
| 2010/0274331 A1 | 10/2010 | Williamson et al. | |
| 2010/0325796 A1 | 12/2010 | Lachenbruch et al. | |
| 2011/0024076 A1 | 2/2011 | Lachenbruch et al. | |
| 2011/0125330 A1 * | 5/2011 | Huber .................. | A61B 5/0002 700/280 |
| 2011/0208541 A1 | 8/2011 | Wilson et al. | |
| 2012/0291200 A1 * | 11/2012 | Dixon ..................... | A61G 7/05 5/600 |
| 2012/0310670 A1 | 12/2012 | Pruitt | |
| 2013/0023215 A1 | 1/2013 | Wang | |
| 2013/0038263 A1 | 2/2013 | Faucher et al. | |
| 2013/0104906 A1 * | 5/2013 | Richards .............. | A61H 9/0078 128/845 |
| 2013/0135160 A1 | 5/2013 | Dixon et al. | |
| 2013/0298330 A1 | 11/2013 | Lachenbruch et al. | |
| 2014/0059766 A1 | 3/2014 | Gibson et al. | |
| 2014/0196210 A1 | 7/2014 | Lachenbruch et al. | |
| 2014/0266735 A1 | 9/2014 | Riggio et al. | |
| 2015/0221202 A1 * | 8/2015 | Russell ................ | G08B 21/0446 340/573.7 |
| 2016/0125716 A1 | 5/2016 | Ribble et al. | |

OTHER PUBLICATIONS

Hill-Rom Services, Inc., Progressa™ Bed Service Manual (2003) (190 pages).
EP Search Report for Application No./Patent No. 15190831.6, dated Mar. 16, 2016 (6 pages).
Extended European Search Report, European Application No. 15190831.6, completed May 7, 2016 (9 pages).

* cited by examiner

EQUIPMENT, DRESSING, AND GARMENT WIRELESS CONNECTIVITY TO A PATIENT BED

The present application is a continuation of U.S. application Ser. No. 14/879,179, filed Oct. 9, 2015, now U.S. Pat. No. 9,711,029, which claimed the benefit, under 35 U.S.C. § 119(e), of U.S. Provisional Application No. 62/073,098, filed Oct. 31, 2014, and each of which is hereby incorporated by reference herein in its entirety.

BACKGROUND

The present disclosure relates to patient beds that communicate with other devices and particularly, to patient beds that communicate wirelessly with other devices. More particularly, the present disclosure relates to patient beds that have wireless readers that read signals from other patient care devices.

Patient beds having mattresses with air bladders that are inflated and deflated so as to reduce the possibility of formation of pressure ulcers are known. Some mattresses include system to determine interface pressures and produce pressure maps so that areas of high pressure are able to be determined. Sometimes bladders beneath the areas of high interface pressure are deflated. However, if a pressure ulcer has already formed, the area of high pressure as sensed by the interface pressure sensing system may or may not correlate to the actual location of the wound. Wound healing is enhanced if pressure on the wound is minimized. Some known pressure minimization techniques include use of specialized patient support equipment and/or the placement of the patient in awkward and uncomfortable positions.

It is also known that patients having particular medical conditions may wear particular garments. For example, patients who are at an elevated risk of falling sometimes wear red colored booties, or so-called "red socks," on their feet so that caregivers are able to quickly identify such patients as falls risks. Some hospital beds are able to implement a falls risk protocol by monitoring whether one or more siderails of the bed are in a raised position, monitoring whether a height of an upper frame of the bed relative to a base frame or floor is in a lowered position, and/or monitoring whether one or more casters of the bed are braked. Some beds may also have a bed exit or patient position monitoring (ppm) system enabled as part of a falls risk protocol so that an alarm or alert is generated in response to a patient exiting the bed or attempting to exit the bed or otherwise moving in the bed by a threshold amount.

Use of wireless communication equipment is becoming more common on patient beds. Accordingly, use of such equipment to improve upon pressure reduction capabilities of patient beds and to improve upon implementation of falls risk protocols would be appreciated by caregivers. Use of wireless communication equipment on a patient bed for other purposes such as insuring proper compatibility of the bed with the particular type of patient or with other types of equipment may also be desirable.

SUMMARY

The present application discloses one or more of the features recited in the appended claims and/or the following features which, alone or in any combination, may comprise patentable subject matter:

According to an aspect of this disclosure, a system may include a patient bed that may have at least one reader to receive wireless signals. The patient bed may also have a mattress that may include a plurality of inflatable sections and a pneumatic system that may control inflation of the plurality of inflatable sections. The system may further include a wound dressing that may have a transmitter that may emit a wireless dressing signal that may be read by the reader. The pneumatic system may adjust mattress inflation in response to receipt of the wireless dressing signal by the at least one reader.

The pneumatic system may, for example, adjust mattress inflation by deflating a first inflatable section of the plurality of inflatable sections. It is contemplated that the first inflatable section may be located beneath the wound dressing. The pneumatic system may deflate multiple inflatable sections in a vicinity of the mattress beneath the wound dressing in some embodiments. The deflation of the multiple inflatable sections may be by different amounts.

In some embodiments, the at least one reader may include a matrix of readers. The patient bed may include control circuitry that may determine an X coordinate and a Y coordinate with respect to the bed of the location of the wound dressing. A graphical display may be coupled to the control circuitry and may show a graphical representation of the location of the wound dressing. The graphical representation may include an image of a patient and the location of the wound dressing may be superimposed on the image of the patient. The image of the patient may comprise a pressure map.

In some embodiments, the plurality of inflatable sections of the mattress may include a matrix of inflatable sections. Each reader of the matrix of readers may correspond to a respective inflatable section of the plurality of inflatable sections. The at least one reader may comprise a radio frequency identification (RFID) reader and the transmitter may comprise a component of an RFID tag. Alternatively or additionally, the at least one reader may comprise a near field communication (NFC) reader and the transmitter may comprise a component of an NFC tag.

According to this disclosure, the dressing may include a pressure sensor and the transmitter may be signaled to emit the wireless dressing signal in response to the pressure sensor sensing that the wound dressing is bearing a threshold amount of weight. The wireless dressing signal may include data indicative of a wound type on which the dressing is being used. The pneumatic system may adjust mattress inflation differently depending upon the wound type. The wireless dressing signal may include data indicative of a location on a patient's body at which the wound dressing is placed.

According to another aspect of this disclosure, a system may include a bed that may have at least one reader to receive wireless signals and that may have a patient position monitoring system that, when in an enabled state, may alarm in response to at least one of the following: a patient exiting the bed or a patient moving toward exiting the bed by a threshold amount. The system may further include a garment that may have a transmitter that may emit a wireless garment signal that may be read by the reader. The patient position monitoring system may change from a disabled state to an enabled state in response to receipt of the wireless garment signal by the at least one reader.

In some embodiments, the garment may comprise at least one sock that may be worn by a patient. For example, the sock may be color coded to indicate that the patient may be a falls risk. The sock may be color coded red if desired.

In some embodiments, the bed may include a brake sensor to sense whether at least one caster of the bed is braked. The bed may further have control circuitry that may be configured to implement a fall prevention protocol in response to receipt of the wireless garment signal by the at least one reader. The fall prevention protocol may include initiating an alert if the brake sensor indicates that the at least one caster is not braked.

Alternatively or additionally, the bed may include at least one siderail position sensor to sense whether at least one siderail of the bed is in a raised position. The bed may further have control circuitry that may be configured to implement a fall prevention protocol in response to receipt of the wireless garment signal by the at least one reader. The fall prevention protocol may include initiating an alert if the at least one siderail position sensor indicates that the at least one siderail is not in the raised position.

Further alternatively or additionally, the bed may include at least one frame position sensor to sense whether an upper frame of the bed is in a lowered position. The bed may further have control circuitry configured to implement a fall prevention protocol in response to receipt of the wireless garment signal by the at least one reader. The fall prevention protocol may include initiating an alert if the at least one frame position sensor indicates that the upper frame is not in the lowered position.

In some embodiments, the system may further include a computer device that may be remote from the bed. The bed may include a brake sensor to sense whether at least one caster of the bed is braked. The bed may further have bed circuitry and the bed circuitry may send to the computer device brake status data that may indicate whether the at least one caster is braked. The bed circuitry may also send to the computer device notification data that may indicate that the reader has received the wireless garment signal. The computer device may be configured to implement a fall prevention protocol in response to receipt of the notification signal. The fall prevention protocol may include initiating an alert if the brake status data indicates that the at least one caster is not braked.

Alternatively or additionally, the system may further include a computer device that may be remote from the bed. The bed may include at least one siderail position sensor to sense whether at least one siderail of the bed is in a raised position. The bed may further have bed circuitry and the bed circuitry may send to the computer device siderail status data that may indicate whether the at least one siderail is raised. The bed circuitry may also send to the computer device notification data that may indicate that the reader has received the wireless garment signal. The computer device may be configured to implement a fall prevention protocol in response to receipt of the notification signal. The fall prevention protocol may include initiating an alert if the siderail status data indicates that the at least one siderail is not in the raised position.

Further alternatively or additionally, the system may further include a computer device that may be remote from the bed. The bed may include at least one frame position sensor to sense whether an upper frame of the bed is in a lowered position. The bed may further have bed circuitry and the bed circuitry may send to the computer device frame status data that may indicate whether the upper frame is in the lowered position. The bed circuitry may send to the computer device notification data that may indicate that the reader has received the wireless garment signal. The computer device may be configured to implement a fall prevention protocol in response to receipt of the notification signal. The fall prevention protocol may include initiating an alert if the frame status data indicates that the upper frame is not in the lowered position.

According to still another aspect of the present disclosure, a system for determining if medical equipment is entering or exiting through a doorway of a room in a healthcare facility is provided. The system may include a first passive tag that may emit a first wireless signal. The first passive tag may be mounted adjacent the doorway outside the room. The system may also include a second passive tag that may emit a second wireless signal. The second passive tag may be mounted adjacent the doorway inside the room. The system may further include a piece of medical equipment that may have circuitry to receive the first and second wireless signals. The circuitry may be configured with software that determines that the piece of medical equipment is entering the room if the first wireless signal is received prior to the second wireless signal being received and that determines that the piece of medical equipment is exiting the room if the second wireless signal is received prior to the first wireless signal being received.

In some embodiments, the system may further include a third passive tag that may emit a third wireless signal that may include room identification data. The circuity may also receive the third wireless signal. In some embodiments, the system may further include a third passive tag that may emit a third wireless signal that may include patient identification data. The circuitry also receiving the third wireless signal. Embodiments in which one additional tag may emit a wireless signal that may have room ID data and another additional tag may emit a wireless signal that may have patient ID data are contemplated by this disclosure and the circuitry of the bed may receive the signals from one or both of the additional tags.

In some embodiments, the piece of medical equipment may comprise a patient bed. The system may further include a third passive tag that may emit a third wireless signal that may include room identification data. The circuity may also receive the third wireless signal and the software may make a bed-to-room association that may be communicated from the patient bed to at least one remote computer device. Alternatively or additionally, the third passive tag may emit a third wireless signal that includes patient identification data. The circuity may also receive the third wireless signal and the software may make a bed-to-patient association that may be communicated from the patient bed to at least one remote computer device. Further alternatively or additionally, the third passive tag may emit a third wireless signal that may include mattress identification data. The circuity may also receive the third wireless signal and the software may make a bed-to-mattress association that may be communicated from the patient bed to at least one remote computer device.

In some embodiments, the system further includes a second piece of medical equipment that may carry a third passive tag that may emit a third wireless signal that may include device identification data. The circuity may also receive the third wireless signal and the software may make a bed-to-device association that may be communicated from the patient bed to at least one remote computer device.

According to still a further aspect of this disclosure, a system may include a patient bed that may include a reader. The patient bed may also include a weigh scale system that may be operable to measure a weight of a patient. The system may further include a patient identification (ID) transmitter to be worn by a patient. The patient ID transmitter may transmit a wireless signal that may be read by the reader. The system also may include a computer that may be remote from the patient bed. The patient bed may transmit to the computer patient ID data that may be determined from the wireless signal. The patient bed may transmit weight data that may correspond to the weight of the patient. The computer may initiate a first alert if the weight data indicates that the patient weighs more than a weight rating of the patient bed.

In some embodiments, the system may further include a patient lift that may have a lift ID transmitter that may transmit a lift ID. The lift ID may be read by the reader of the patient bed and may be transmitted to the computer. The computer may initiate a second alert if the weight data indicates that the patient weighs more than a weight rating of the lift.

The alerts mentioned above may comprise a transmission to a wireless communication device of an assigned caregiver and/or an alert message on a display of the computer. Furthermore, the alerts mentioned above may comprise any one or more of the following: an audible alert, a visual alert, or a tactile alert.

According to this disclosure, the system may further include a mattress and a mattress ID transmitter may be associated with the mattress. The mattress ID transmitter may transmit a mattress ID that may be read by the reader of the patient bed. The patient bed may transmit the mattress ID to the computer. The computer may initiate an alert if the mattress is not suitable for the patient based on pressure ulcer risk assessment data associated with the patient. The pressure ulcer risk assessment data may be received by the computer from another computer, for example.

According to yet another aspect of the present disclosure, a system for use with an electronic medical records (EMR) computer is provided. The system may include a patient bed that may include a reader. The system may have a patient identification (ID) transmitter to be worn by a patient. The patient ID transmitter may emit a wireless signal that may be read by the reader. The system may further have a computer that may be remote from the patient bed and that may be remote from the EMR computer. The patient bed may transmit to the computer patient ID data that may be determined from the wireless signal. The computer may receive from the EMR computer weight data corresponding to the weight of the patient. The computer may initiate a first alert if the weight data indicates that the patient weighs more than a weight rating of the patient bed.

In some embodiments, the computer may transmit the patient ID data to the EMR computer. In some embodiments, the system may further include a patient lift that may have a lift ID transmitter that may transmit a lift ID. The lift ID may be read by the reader of the patient bed and may be transmitted to the computer. The computer may initiate a second alert if the weight data indicates that the patient weighs more than a weight rating of the lift.

According to this disclosure, the alerts just mentioned may comprise a transmission to a wireless communication device of an assigned caregiver or an alert message on a display of the computer. Furthermore, the alerts just mentioned may comprise one or more of the following: an audible alert, a visual alert, or a tactile alert.

In some embodiments, the system may further includes a mattress and a mattress ID transmitter may be associated with the mattress. The mattress ID transmitter may transmit a mattress ID that may be read by the reader of the patient bed. The patient bed may transmit the mattress ID to the computer. The computer may initiate a second alert if the mattress is not suitable for the patient based on pressure ulcer risk assessment data associated with the patient. The pressure ulcer risk assessment data may be received by the computer from the EMR computer, for example.

Additional features, which alone or in combination with any other feature(s), such as those listed above and/or those listed in the claims, may comprise patentable subject matter and will become apparent to those skilled in the art upon consideration of the following detailed description of various embodiments exemplifying the best mode of carrying out the embodiments as presently perceived.

BRIEF DESCRIPTION OF THE DRAWINGS

The detailed description particularly refers to the accompanying figures in which.

DETAILED DESCRIPTION

Figure 1:
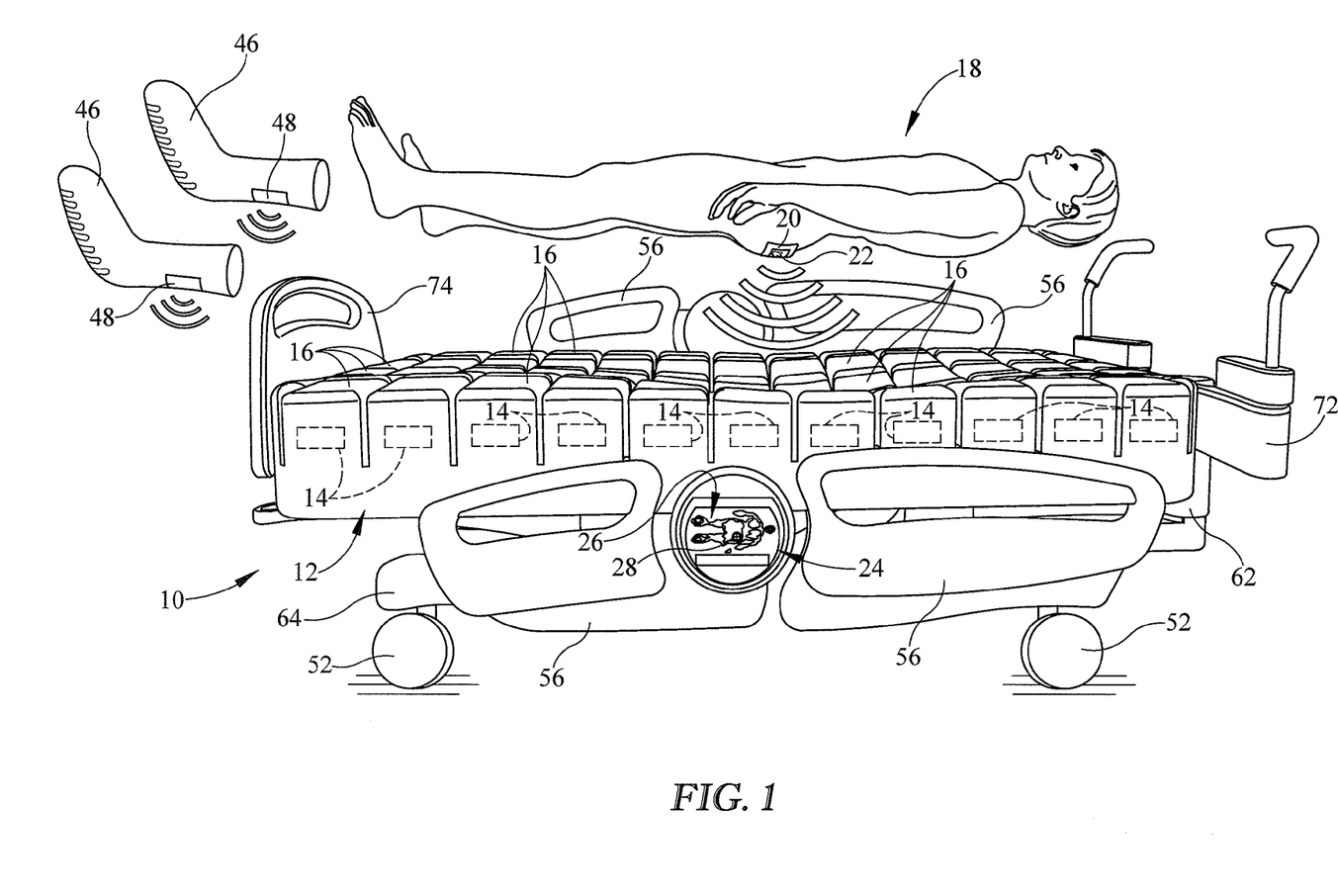
FIG. 1 is a perspective view showing a wound dressing transmitting a wireless signal toward a patient bed, showing a graphical display of the patient bed displaying a location of the wound dressing on a pressure map of the patient, and showing falls prevention socks arranged for coupling to the patient's feet with one of the falls preventions socks having a tag transmitting a wireless signal toward the patient bed.

Referring now to FIG. 1, a patient bed 10 includes an inflatable mattress or surface 12 having a plurality of wireless interrogators or transceivers 14. Transceivers 14 include receivers or readers as well as transmitters. However, in some embodiments, bed 10 includes a plurality of readers without any transmitters. Thus, the discussion below of embodiments of bed 10 having transceivers 14 is equally applicable to beds 10 having readers (or receivers) rather than transceivers unless specifically noted otherwise. Each transceiver 14 is situated within or beneath an associated inflatable section 16 of mattress 12. In some embodiments, the inflatable sections 16 are bladders or cells, for example, that are arranged in columns in a longitudinal dimension (i.e., head end to foot end) of bed 10 and that are arranged in rows in a lateral dimension (i.e., side to side) of bed 10. Thus, the sections 16 and transceivers 14 form an X-Y grid or matrix when mattress 12 is viewed from above.

In the illustrative example, there are eleven bladders 16 in the longitudinal dimension of mattress 12 and four bladders 16 in the lateral dimension of mattress 12. Thus, the X-Y grid is either a 4 by 11 grid or an 11 by 4 grid of bladders, as desired, in the illustrative example. Of course, X-Y grids or matrices having other numbers of bladders 16, and corresponding transceivers 14, greater than or less than four and/or greater than or less than eleven are within the scope of this disclosure. Furthermore, while the illustrative bladders 16 have generally square-shaped cross sections in horizontal planes, bladders having other cross-sections such as circular, rectangular, triangular, hexagonal, octagonal, and even irregular-shaped are within the scope of this disclosure as are combinations of these.

As shown diagrammatically in FIG. 1, a patient 18 is suspended above an upper surface of mattress 12 for ease of illustration and discussion. A dressing or bandage 20 is applied to a pressure ulcer of the patient 18 or to a region that is at risk of developing a pressure ulcer (hereinafter referred to collectively as a "pressure ulcer region"). In the illustrative example, the pressure ulcer region and therefore, the dressing 20, are located on the patient's left buttock. However, this location of dressing 20 is simply one example of a typical high pressure location at which pressure ulcer regions occur on a patient. Other locations include the patient's heels, sacral region, scapula, and occiput. That is, pressure ulcer regions of the patient 18 are typically associated with portions of the patient's body having bony protuberances but this is not always the case.

According to this disclosure, dressing 20 includes a wireless transmitter 22 such as one that is included in a radio frequency identification (RFID) tag or a near field communication (NFC) tag. Because RFID tags and NFC tags are well-known in the art, reference number 22 is used in the Figs. for purposes of denoting all types of wireless transmitters as well as RFID tags and NFC tags. In some embodiments, the RFID/NFC tags 22 are passive tags that respond by transmitting or emitting wireless identification (ID) data in response to a signal sent by transceivers 14. The reception range of tags 22 is short range, such as on the order of about 10 centimeters (cm), in some embodiments. In other embodiments, transmitters 22 are active transmitters that periodically transmit or emit the wireless ID data. In such embodiments, bed 10 need only have receivers rather than transceivers 14.

In use, transceivers 14 send out interrogation signals periodically and, in response to receipt of the interrogation signals, transmitter 22 of dressing 20 responds by transmitting the ID data. One or more of transceivers 14 receive this ID data transmitted from dressing 20. This process is sometimes referred to as a "handshake." If only one of transceivers 14 receives the ID data, then that particular transceiver 14 or cell 16 is designated as the zero point (x, y coordinates) of the wound or pressure ulcer region on the X-Y grid. If more than one transceiver 14 receives the ID data, then the zero point (x, y coordinates) is determined by averaging the X-Y grid coordinates of the individual transceivers 14 or cells 16 that receive the ID data.

Still referring to FIG. 1, bed 10 includes a graphical user interface (GUI) 24 that, in the illustrative example, displays a pressure map 26 having colored regions that are indicative of the interface pressure between the patient 18 and mattress 12. Pressure map 26 also provides information about pressure gradients between the patient 18 and mattress 12. The pressure map 26 is generated based on pressure readings from pneumatic pressure sensors associated with each of cells 16 in some embodiments, for example. Alternatively or additionally, the pressure map 26 is generated based on pressure readings from a sensor layer (not shown) that is placed between the patient 18 and mattress 12. Such pressure sensor layers are known in the art. See for example, U.S. Pat. Nos. 5,010,772; 5,253,656; 6,585,328; and 8,272,276 which are hereby referenced herein to the extent not inconsistent with the present disclosure which shall control as to any inconsistencies. In still other embodiments, pressure sensors are included on or near the upper surfaces of cells 16 and the readings from such sensors are used in generating pressure map 26. See, for example, U.S. Pat. No. 7,409,735 which is hereby incorporated by reference herein to the extent not inconsistent with the present disclosure which shall control as to any inconsistencies.

In other embodiments, some other type of image of the patient 18 is shown on the GUI 24 in lieu of or in addition to the pressure map. For example, a generic patient avatar is used as the image in some embodiments. Superimposed on the pressure map 26 or other patient image is an icon 28 that indicates the location of dressing 20 on the patient 18. The location of icon 28 on the pressure map 26 corresponds to the x-y coordinates or zero point of the dressing 20 as determined by the ID data received by one or more of transceivers 14 from transmitter 22 of dressing 20.

In FIG. 1, the location of icon 28 on pressure map 26 is in the region of the patient's left buttock which corresponds to the actual location of dressing 20 on patient 18 in FIG. 1. In contrast, in FIG. 2, icon 28 on pressure map 26 appears in the region of the patient's left thigh which corresponds to the actual location of dressing 20 on patient 18 in FIG. 2. Also in FIG. 2, each transceiver 14 of mattress 12 is illustrated as being located in a base layer or region of mattress 12 rather than up in individual cells 16 of mattress 12 as is the case in FIG. 1. As indicated diagrammatically in FIG. 3, a further variant is to have the transceivers 14 located outside of the mattress 12 altogether, such as being mounted to a patient support deck of bed 10 which supports mattress 12.

Regardless of the location of transceivers 14, once the zero point location of the dressing 20 relative to the associated X-Y grid of transceivers 14 is determined, pressures within certain bladders 16 of mattress 12 are adjusted. For example, in some embodiments, a cell 16 directly beneath dressing 20 is deflated by some amount. The amount of deflation is dependent upon mattress geometry but suffice it to say that the target pressure for the cell 16 beneath dressing 20 is reduced from a first target pressure to a second target pressure.

In some embodiments, one or more of the cells 16 adjacent to the cell 16 that is directly beneath the dressing 20 are also deflated by some amount, but not as much as the "zero point" cell 16 in some embodiments. For example, if the "zero point" cell is deflated by an amount delta, the next adjacent cells are deflated by ½ delta in some embodiments. Fractions above and below ½ delta are, of course, within the scope of this disclosure. Also, cells 16 that are situated diagonally from the corners of the "zero point" cell are deflated at delta fractions different than those of the cells that are directly longitudinally adjacent and directly laterally adjacent to the "zero point" cell in some embodiments. In a variant embodiment, only those cells 16 associated with transceivers 14 that perform a handshake with transmitters 22 of dressing 20 are deflated from a first target pressure to a second target pressure, which second target pressures may vary from cell to cell depending upon distance from the zero point cell 16 if desired. Based on the foregoing, it should be appreciated that the interface pressure between the patient 18 and mattress 12 is reduced as a result of deflation of the cells 16 that are in the immediate area of the wound dressing 20 as determined by the communication between transceivers 14 and transmitters 22 of dressing 20.

It is also within the scope of this disclosure for the amount of pressure reduction (e.g., cell deflation) to be controlled based on the type and/or stage of the wound on which dressing 20 is used. The information regarding the type and/or stage of the wound is entered into the control system of bed 10 or mattress 12 by a caregiver in some embodiments, such as by use of GUI 24. Alternatively or additionally, the information regarding the type and/or stage of the wound is downloaded to the control system of bed 10 or mattress 12 from a remote computer, such as a computer of an electronic medical records (EMR) system in other embodiments. In still other embodiments, the ID data emitted by transmitter 22 of dressing 20 includes data that indicates the type and/or stage of the wound that bandage 20 covers. Alternatively or additionally, the ID data emitted by transmitter 22 indicates the location of dressing on the patient 18. For example, a dressing 20 configured for use on a patient's heel emits data different than a dressing configured for use on a patient's sacral region, just to give a couple examples. Thus, dressings 20 that are designated for wounds of specific types and/or stages and/or locations are within the scope of this disclosure and are selected by caregivers so that the proper type of ID data is transmitted to the transceivers 14 of bed 10 from dressing 20. Examples of types of wounds include burns, pressure ulcers, lacerations, and avulsions, just to name a few. Examples of stages of wounds include, for example, first degree burns, second degree burns, third degree burns, stage I pressure ulcers, stage II pressure ulcers, stage III pressure ulcers, and stage IV pressure ulcers, just to name a few.

Figure 3:
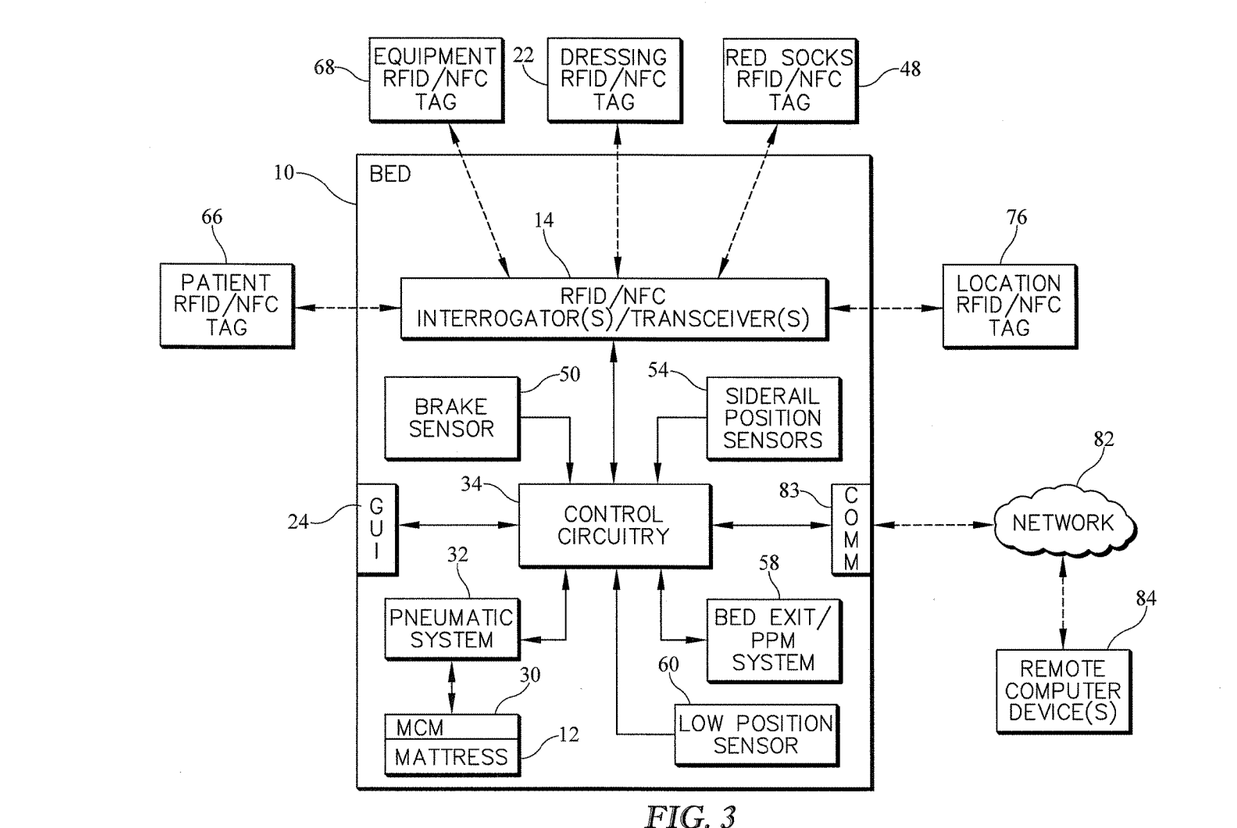
FIG. 3 is a block diagram showing the circuitry of the patient bed including one or more radio frequency identification (RFID)/near field communication (NFC) Interrogators/Transceivers in communication with one or more patient, equipment, dressing, red socks, and location RFID/NFC tags.

Further according to this disclosure, a microclimate management (MCM) layer of mattress 12 is controlled depending upon the location of dressing 20, the type of wound, and/or the stage of wound. In FIG. 3, mattress 12 is shown diagrammatically as including an MCM layer 30. However, MCM layers are known in the art. See, for example, U.S. Patent Application Publication Nos. 20100274331; 20100325796; 20110024076; 20130298330; 20140059766 and 20140196210; each of which is hereby incorporated by reference herein to the extent not inconsistent with the present disclosure which shall control as to any inconsistencies.

With regard to localized MCM systems (e.g., those that are able to heat or cool a specific region of a patient's body), the temperature or thermal heat exchange to or from the region of the patient 18 at which dressing 20 is located is controlled differently than at other regions of the patient's body in some embodiments according to this disclosure. For example, some types of wounds at some stages may benefit from localized cooling whereas other types of wounds at other stages may benefit from localized heating. With regard to airflow type of MCM systems (e.g., those that move temperature and/or humidity controlled air through a layer beneath the patient 18 at controlled volumes and/or flow rates), the temperature and/or humidity and/or volume and/or flow rate of the air through the entire MCM layer, or through a localized portion of the layer beneath dressing 20, is controlled based on wound location, wound type, and/or wound stage. For example, some types of wounds at some stages may benefit from slow moving, warm, moist air and other types of wounds at other stages may benefit from fast moving, cool, dry air, just to provide a couple of examples.

When it is stated that a wound "may benefit from" some particular set of parameters, it is intended to mean that wound healing is enhanced by the set of parameters. Control of all combinations and permutations of the above-referenced MCM parameters in the region beneath dressing 20 to promote wound healing is within the scope of this disclosure. In still other embodiments, it is contemplated that the MCM feature is disabled in the region beneath dressing 20 and enabled in other regions away from the location of the wound. All combinations of MCM control and pressure control (e.g., bladder 16 deflation), as described above, are also contemplated by this disclosure.

Thus, bed 10 includes a pneumatic system 32 which is controlled by control circuitry 34 as shown diagrammatically in FIG. 34. It will be appreciated by those skilled in the art that pneumatic systems and control circuitry of patient beds are complex in nature and that these are shown in the present disclosure in a simplified rudimentary manner. However, additional details of one example of such a pneumatic system and control circuitry for a patient bed can be found in *SERVICE MANUAL, Progressa™ Bed, From Hill-Rom,* ©2013, which is hereby incorporated by reference herein to the extent not inconsistent with the present disclosure which shall control as to any inconsistencies. It will be appreciated that it is the addition of the transceivers 14 to the bed 10 and/or mattress 12 as well as the other components (e.g., dressing 20) that communicate with transceivers 14 which are the primary focus of the present disclosure.

Figure 5:
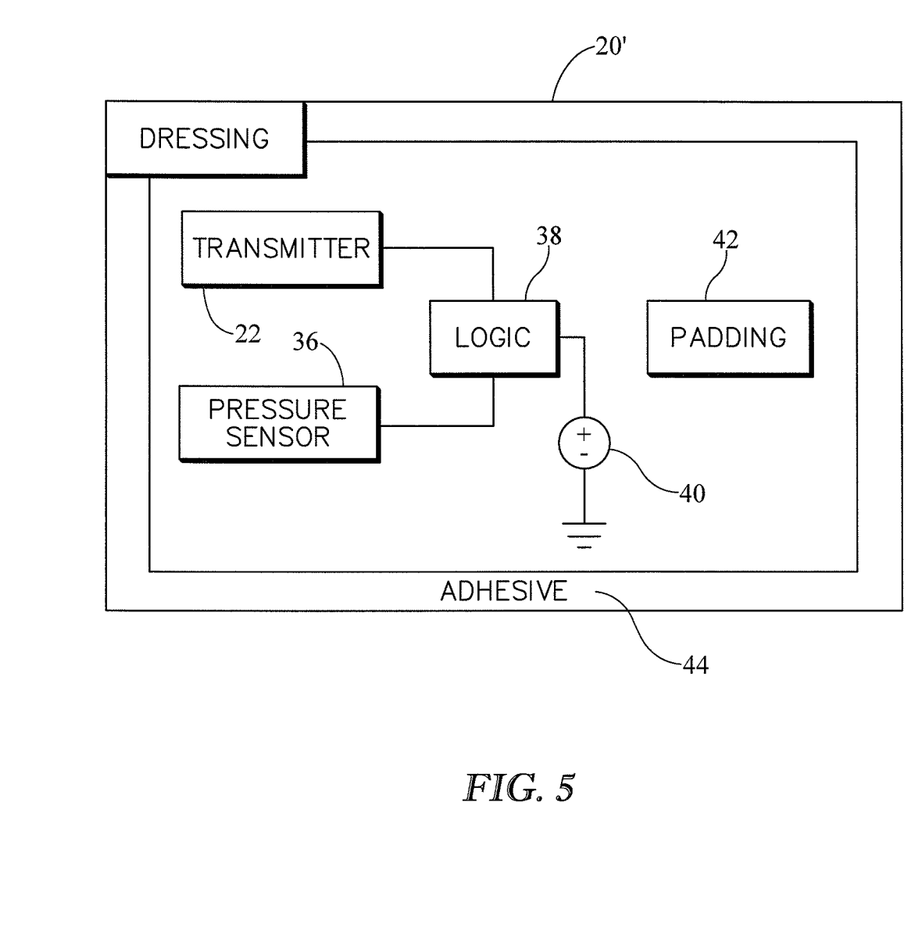
FIG. 5 is a diagrammatic view of a wound dressing having a pressure sensor and transmitter that is signaled by a logic circuit to transmit a wireless signal in response to the pressure sensor sensing a threshold amount of weight bearing on the wound dressing.

Referring to FIG. 5, an alternative dressing 20' is shown diagrammatically in which a pressure sensor 36, logic 38, and battery 40 are included in addition to transmitter 22. Also shown diagrammatically in dressing 20' in FIG. 5 are padding 42 and peripheral adhesive 44 but these are inherent in the contemplated dressings anyway. According to this disclosure, transmitter 22 of dressing 20' does not transmit any ID data until pressure sensor 36 senses that dressing 20 is bearing a threshold amount of weight as determined by logic 38. For example, logic 38 includes a comparator circuit in some embodiments and when a voltage output by pressure sensor 36 exceeds a preset voltage level, transmitter 22 is signaled by circuit 38 to transmit the ID data. In some such embodiments, pressure sensor 36 comprises a force sensitive resistor (FSR), piezoresistive sensor, or capacitive type sensor with a voltage output that varies depending upon the amount of applied weight.

In other embodiments, pressure sensor 36 comprises a contact switch. In such embodiments, when a threshold amount of weight is applied to the switch, contact is made between switch elements so that the switch changes from an open or off state to a closed or on state. Some sort of bias element such as a spring, foam pad, rubber pad or other compressible element is provided between the switch elements in some embodiments to establish the amount of weight that must be applied to the switch element before contact therebetween is made. Once contact is made between the switch element, current flows through the switch to logic circuit 38 which, in turn, signals transmitter 22 to emit the ID data from dressing 20'.

Regardless of the type of pressure sensor 36 used, pressure and/or MCM adjustments to mattress 12 are made only if the patient 18 moves to a position in which dressing 20' bears the threshold amount of weight in the embodiments in which dressing 20' is used. For example, if a patient is lying on his or her side with no weight, or very little weight, bearing on dressing 20', there is no need to make adjustments to mattress 12 for purposes of promoting wound healing (e.g., but adjustments may still be made for other reasons). However, if a patient rolls into a position in which dressing 20' becomes weight bearing, the transmission of ID data from transmitter 22 of dressing 20' signals circuitry 34 via transceivers 14 to control pneumatic system 32 in the appropriate manner as describe above to make the adjustments to mattress 12 to promote wound healing.

It is within the scope of this disclosure that a historical database of clinical wound data, such as wound location, type and/or stage, as well as types of dressing 20, 20' used and the duration of use of each during treatment of the patient's wound(s), is maintained in control circuitry 34 of bed 10 in some embodiments. Alternatively or additionally, some or all of this same information is communicated for storage via a network 82 to one or more remote computer devices 84 as shown diagrammatically in FIG. 3. Thus, bed 10 has a communication port or module 83 as shown diagrammatically in FIG. 3 for communication of data to and from bed 10. In some embodiments, port 83 is a cable connector, such as a 37-pin connector port which is well known in the art. Alternatively or additionally, module 83 includes wireless communication circuitry such as circuitry for WiFi or RF communications (e.g., Bluetooth, Zigbee, 802.11, etc.).

Remote computer devices 84 include an EMR computer, for example. Analysis of the historical data is useful in implementing further pressure control protocols and regimens of mattress 12 during the patient's stay to prevent additional pressure ulcers from developing. Furthermore, accumulation of this historical data for a number of patients allows for subsequent analysis to determine pressure control protocols and regimens for mattress 12 for future patients and to make predictions regarding potential pressure ulcer development for future patients so that preventative measures are taken ahead of time to reduce the likelihood for pressure ulcer development for future patients.

Referring once again to FIGS. 1 and 2, a pair of socks 46 or booties are shown adjacent the patient's feet. Socks 46 are so-called "red socks" that are worn by patients who are determined to be falls risks. However, unlike the prior art "red socks," socks 46 include transmitters 48 that emit wireless signals including socks or garment ID information that identify the patient as a falls risk. Transmitters 48 are included as part of an RFID tag or an NFC tag in some embodiments. Furthermore, although each of socks 46 is shown as including a respective transmitter 48 in the illustrative example, it is within the scope of this disclosure for only one of socks 46 to include transmitter 48 and, it matters not whether it is the left sock or right sock that includes transmitter 48, as long as one of transceivers 14 of bed 10 is able to communicate wirelessly with the transmitter 48.

Figure 2:
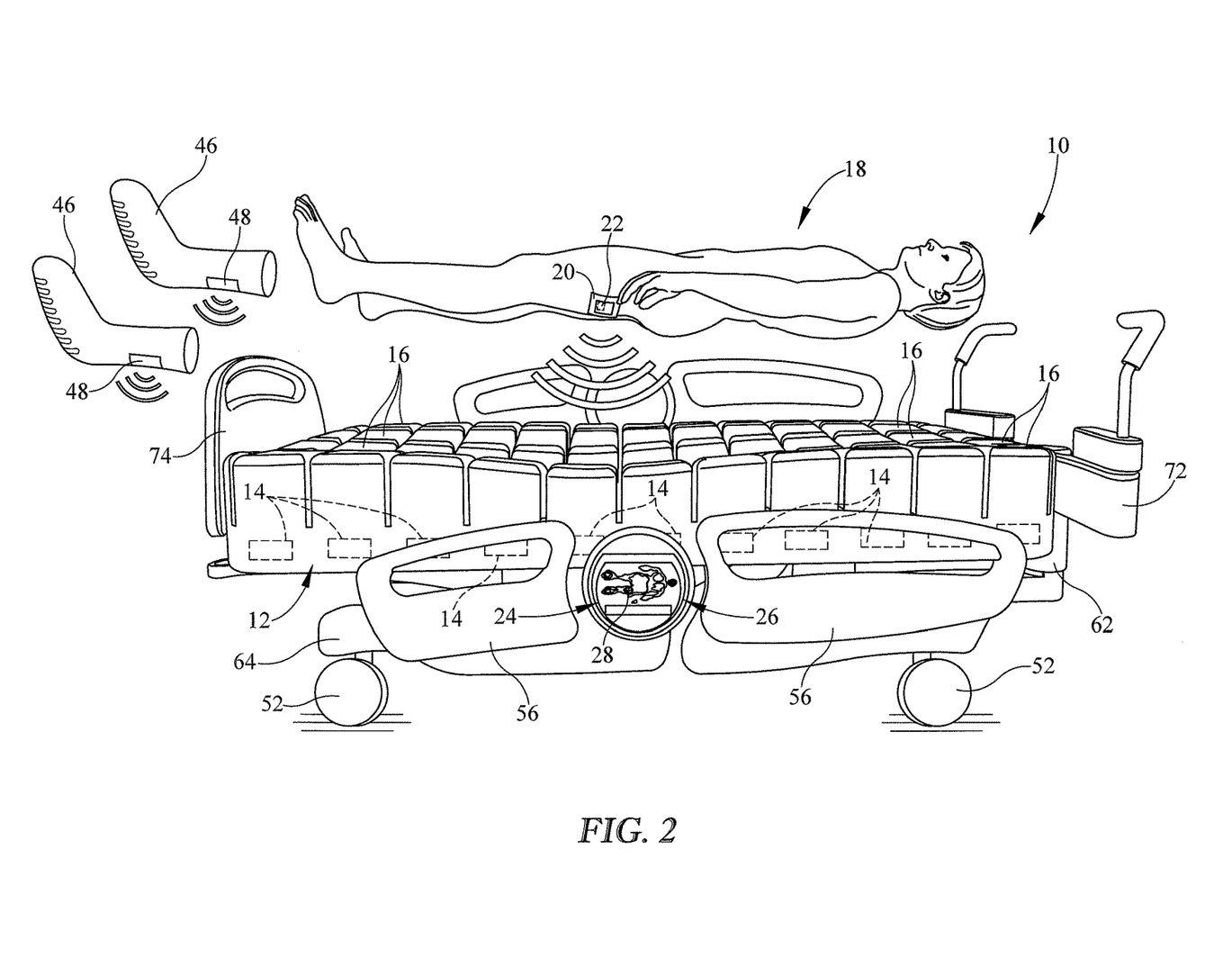
FIG. 2 is a perspective view similar to FIG. 1 but showing another wound dressing at another location on the patient's body.

For patients who are falls risks, caregivers sometimes manually implement a falls risk protocol in connection with an associated patient bed. For example, one falls risk protocol for a patient bed requires that casters of the bed are braked, that siderails of the bed are in a raised position, that a bed exit/ppm system of the bed is armed, and that an upper frame of the bed is in a lowered position relative to a base frame of the bed. So, in keeping with such a protocol in the illustrative example, bed 10 has a brake sensor 50 to sense whether casters 52 of bed 10 are braked or released, siderail position sensors 54 to sense whether respective siderails 56 of bed 10 are in raised positions or lowered positions, a bed exit/ppm system 58 to sense whether the patient had exited the bed 10 and/or to sense the patient's position in bed 10 to determine if the patient is moving toward exiting the bed, and a low position sensor 60 to sense a position of an upper frame 62 of bed 10 relative to a base frame 64 of bed 10. Sensors 50, 54, 60 and system 58 are shown diagrammatically in FIG. 3 and the corresponding structures 52, 56, 62, 64 are shown in FIGS. 1 and 2. In some embodiments, sensor 60 comprises multiple sensors, such as potentiometers or rotary encoders, that are included in linear actuators of a lift system (not shown) of bed 10. Linear actuators having such sensors 60 are well known in the art.

According to the present disclosure, control circuitry 34 of bed 10 implements the falls risk protocol for bed 10 automatically in response to any one or more of transceivers 14 receiving socks ID data from one or both of transmitters 48 of garments 46. Furthermore, in some embodiments, bed 10 notifies one or more remote computer devices 84 via network 82 that the remote falls risk protocol has been implemented automatically at bed 10. If the one or more of remote computer devices 84 receiving the notification from bed 10 also have a falls risk protocol, that too is implemented automatically in response to the notification from bed 10. See U.S. Pat. No. 7,319,386 which is hereby incorporated by reference herein to the extent not inconsistent with the present disclosure which shall control as to any inconsistencies for an example of a nurse call computer which implements a Fall Prevention (e.g., falls risk) protocol.

In connection with implementing the falls risk protocol automatically, control circuitry 34 of bed 10 automatically enables or arms the bed exit/ppm system of bed 10 so that an alarm is generated if the patient exits the bed and/or moves toward exiting the bed by a threshold amount. If any of the other aspects of bed 10 that are monitored in connection with the falls risk protocol are not in compliance with the protocol, an alert is generated by circuitry 34 of bed 10 and/or by remote computer device 84. Such an alert may include an audible or visual alert, such as a message displayed on GUI 24 to notify a caregiver of any conditions that are out of compliance with the falls risk protocol and that need to be rectified. For example, in FIG. 1, two of the siderails 56 of bed 10 are in the lowered position and so a message on GUI 24 stating; "Raise the Left Foot Rail and Raise the Left Head Rail" is an example of a suitable alert message. Messages pertaining to the other monitored conditions are, of course, within the scope of this disclosure. Such alert messages are also displayed on remote computer device 84 and/or sent from computer device 84 to wireless communication devices carried by assigned caregivers in some embodiments. See U.S. Pat. No. 7,319,386 which is already incorporated by reference herein for examples of such wireless communication devices that are carried by caregivers who are assigned to specific patients.

If a caregiver in the room rectifies a condition that is out of compliance, a message is sent from bed 10 to computer device 44 and the alert at device 84 is canceled and any wireless communication devices carried by assigned caregivers is also notified that the alert condition has been rectified. GUI 24 also ceases to display the associated alert message when the alert condition is rectified. It will be appreciated that the automatic implementation of the falls risk protocol by bed 10 and/or computer device 44 is also indicated on any screens of GUI 24 and computer device 44, such as whiteboard screens, status screens, and so forth using suitable icons and/or messages.

In some embodiments, bed exit/ppm system 58 of bed 10 includes load cells that are also used to measure a weight of the patient 18 that is present on bed 10. See U.S. Pat. Nos. 6,208,250; 6,438,776; 6,924,441 and 7,253,366 which are hereby incorporated by reference herein to the extent not inconsistent with the present disclosure which shall control as to any inconsistencies for examples of weigh scale systems of patient beds. According to this disclosure, after system 58 of bed 10 takes a weight reading of the patient 18 supported on bed 10, circuitry 34 and/or one or more of the remote computer devices 84 compares the patient's weight reading to a weight rating of bed 10. If the patient's weight exceeds the weight rating of bed 10, an alert is provided on GUI 24 of bed 10, at computer device(s) 84, and/or on the wireless communication devices carried by caregivers to notify one or more caregivers that the patient is too heavy for bed 10. Alternatively or additionally, if system 58 determines that the patient's weight plus the weight of any equipment carried on bed 10 (e.g., IV pumps, therapy devices, physiological monitoring devices, ventilation equipment, and the like) exceeds the weight rating of bed 10, then a similar notification is provided. In response, caregivers are able to assign the patient 18 to a more suitable bed that has a higher weight rating.

As shown diagrammatically in FIG. 3, the patient 18 wears a patient ID tag 66, such as illustrative patient RFID or NFC tag 66. Such a tag 66 is included as part of a wrist band in some embodiments as indicated diagrammatically in FIG. 4. According to this disclosure, as patient 18 approaches bed 10, one or more of transceivers 14 receives a wireless signal from the transmitter of tag 66 that identifies the patient. Circuitry 34 of bed then retrieves information about patient 10, including patient weight information, from one or more of the remote computer devices 84 via network 82 and communication module or port 83. For example, an EMR computer 84 typically includes patient weight information. If the patient's weight information exceeds the weight rating of bed 10, then an alert is provided on GUI 24 of bed 10, at computer device(s) 84, and/or on the wireless communication devices carried by caregivers to notify one or more caregivers that the patient is too heavy for bed 10. Thus, in this example, the notification regarding the patient exceeding the weight rating of bed 10 is able to occur prior to the patient getting onto bed 10.

Also according to this disclosure, various pieces of equipment have equipment ID tags 68, such as illustrative equipment RFID or NFC tag 68 shown diagrammatically in FIG. 3, attached thereto. It is contemplated that circuitry 34 of bed 10 and/or one or more of remote computer devices 84 check the compatibility of the equipment identified by tags 68 with bed 10, patient 18, or both. To give one example, patient lifts with slings are sometimes used to transfer patients from a patient bed to some other type of patient support apparatus such as a stretcher or wheelchair or is used to transport the patient from the patient bed to a bathroom, for example. Based on the ID data emitted from the equipment tag 68 of a particular patient lift and received by one of transceivers 14 of bed 10, circuitry 34 of bed 10 retrieves information from one or more remote computer devices 84 regarding the weight capacity or rating of the lift. Alternatively or additionally, circuitry 34 includes its own database or lift weight ratings. If the circuitry 34 determines that the weight of the patient on bed 10, either as measured by system 58 of bed 10 or as indicated by weight information retrieved by circuitry 34 from one or more of devices 84, exceeds the weight rating of the lift, then an alert is provided on GUI 24 of bed 10, at computer device(s) 84, and/or on the wireless communication devices carried by caregivers to notify one or more caregivers that the patient is too heavy for the lift that is in the vicinity of bed 10. Thus, in this example, the notification regarding the patient exceeding the weight rating of the lift is able to occur prior to the patient being loaded onto the lift.

Figure 4:
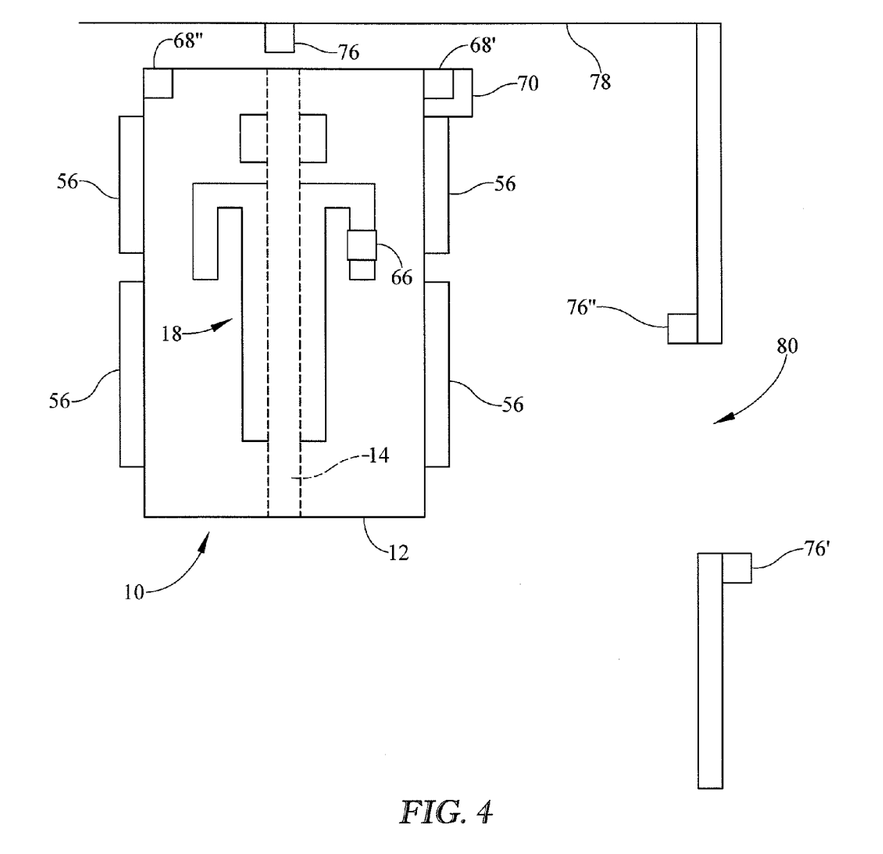
FIG. 4 is another block diagram showing six passive RFID tags that communicate with an RFID reader of the patient bed.

As shown diagrammatically in FIG. 4, one equipment tag 68' is attached to an IV pump 70 and another equipment tag 68" is attached to mattress 12. Circuitry 34 of bed 10 and/or one or more of remote computer devices 84 is able to assess the compatibility of mattress 12 with bed 10 and/or patient 18 based on information about mattress 12 that is determined from the mattress ID information transmitted by tag 68" and received by one or more transceivers 14 of bed 10. For example, if mattress 12 has a size (e.g., thickness, length, and/or width) that would result in an undesirable gap being created between the mattress 12 and any of siderails 56, a headboard 72, or footboard 74, or if the patient's weight exceeds a weight rating of mattress 12, then an alert is provided on GUI 24 of bed 10, at computer device(s) 84, and/or on the wireless communication devices carried by caregivers to notify one or more caregivers that the patient is too heavy for the lift that is in the vicinity of bed 10.

As another example, if patient 18 has particular pressure ulcer risk assessment data or other risk profile data stored in one or more remote computer devices 84, then the compatibility of mattress 12 with patient 18 is determined based on mattress ID data from tag 68" in some embodiments. Thus, mattress ID transmitter 68" transmits a mattress ID that is read by one or more of readers 14 of bed 10. Circuitry 34 of bed 10 then transmits the mattress ID to one or more computer devices 84 via communication port or module 83 and network 82, and the one or more computer devices 84 initiate an alert if mattress 12 is not suitable for the patient 18 based on the pressure ulcer risk assessment data, or other risk profile data, associated with the patient 18. In some embodiments, the pressure ulcer risk assessment data and/or other risk profile data is provided to one or more computer devices 84 from an EMR computer 84. Alternatively or additionally, the EMR computer device 84 is the computer device that assesses the compatibility of mattress 12 for patient 18.

Transceivers 14 of bed 10 are also used in connection with determining the location of bed 10 within a health care facility. The contemplated system uses passive location tags 76, 76', 76" as shown diagrammatically in FIGS. 3 and 4. Thus, the contemplated locating system is less expensive than known prior art locating systems because tags 76, 76', 76" do not require batteries or require extra wires to be routed through a facility. However, due to the short range nature of the passive tags 76, 76', 76", at least one of transceivers 14 of bed 10 needs to be in relatively close proximity (e.g., about 10 cm) for communications to be established. When bed 10 is in use in a patient room supporting patient 18, a head end of bed 10 is usually very close to a room wall 78 (or to a head wall unit mounted to room wall 78) as indicated diagrammatically in FIG. 4. Thus, the location ID data from tag 76 correlates to the room location. If the room is a semi-private room in which two patient beds are located, then two tags 76 are provided, one at each of the two respective room locations which are oftentimes designated as an "A" location and a "B" location (e.g., room 101-A and room 101-B). One or more of transceivers 14 near the head end of bed 10 receives the location ID data from tag 76 and circuitry 34 of bed 10 communicates the bed ID and location ID via communication module or port 83 and network 82 to one or more remote computer devices 84 which maintain a database of bed-to-room associations based on the bed ID and location ID data.

Further according to this disclosure, entry of bed 10 into a patient room and exit of bed 10 from a patient room is determined by use of tags 76', 76". As is evident in FIG. 4, tag 76' is mounted adjacent a room doorway 80 outside the room and tag 76" is mounted adjacent doorway 80 inside the room. As bed 10 enters the room, the wireless signal from tag 76' will be received by one of transceivers 14 of bed 10 slightly earlier in time than the wireless signal from tag 76" will be received, likely by another one of transceivers 14 of bed 10 since tags 76', 76" are on opposite sides of doorway 80 in the illustrative example. If tags 76', 76" were situated on the same side of doorway 80, but still with tag 76' outside of the room and with tag 76" inside of the room, then it would be more likely that the same transceiver 14 of bed would receive the wireless signals from tags 76', 76" as the bed enters or exits the room. There is only a small amount of clearance between the sides of patient beds and the doorways in healthcare facilities and so transceivers 14 near the sides of bed 10 will pass sufficiently close to tags 76', 76" for communications to be established therebetween.

In some embodiments, control circuitry 34 of bed 10 is configured with software that determines that bed 10 is entering the room if the wireless signal from tag 76' is received prior to the wireless signal from tag 76" being received and that determines that bed 10 is exiting the room if the wireless signal from tag 76" is received prior to the wireless signal from tag 76' being received. In such embodiments, circuitry 34 of bed 10 has a database with information regarding the ID's of tags 76' that are located outside of the various rooms and the ID's of tags 76" that are located inside of the various rooms. Alternatively or additionally, one or more remote computer devices 84 include the software that determines whether bed 10 is entering or exiting a room based on the sequence that transceivers 14 of bed 10 receive wireless signals from tags 76', 76". It is within scope of this disclosure for the locations of other pieces of equipment or devices to be determined using tags 76, 76', 76" in a similar manner as described above in connection with bed 10 as long as such other pieces of equipment or devices have readers, receivers, or transceivers 14 like those of bed 10 and have wireless communication capability similar to that provided by circuitry 34 and communication module 83 of bed 10.

Based on the foregoing, it will be appreciated that transceivers 14 of bed 10 communicate with transmitters of equipment tags (e.g., tag 68), garment tags (e.g., tag 48), dressing tags (e.g., tag 22), patient tags (e.g., tag 66), and location tags (e.g., tag 76) as well as others (e.g., tags 68', 68", 76', 76"). Circuitry 34 of bed 10 sends ID data from each of these tags, along with bed ID, to one or more remote computer devices 84. Thus, it is within the scope of this disclosure for the one or more remote computer devices to maintain a database of associations between any and all of these ID's as desired and at the discretion of the system programmer. Thus, a mattress-to-patient-to-IV pump-to-bed-to-location-to-dressing-to-red socks association could be made if desired, just to give one example.

Also according to this disclosure, the duration that one or more of transceivers 14 of bed 10 are in communication with any of equipment tags 68 or other tags disclosed herein is tracked by circuitry 34 and/or one or more computer devices 84 for purposes of determining age, usage hours, cleaning cycles, clean/dirty status, functioning/broken status, and the like. The usage of the equipment is compared to established protocols in some embodiments to determine compliance with the protocols. For example, if dressing 20 is supposed to be changed every 12 hours according to a protocol, then it can be determined that the protocol was violated if bed 10 was in communication with a particular dressing for, say, 14 hours, just to give one example.

Although certain illustrative embodiments have been described in detail above, variations and modifications exist within the scope and spirit of this disclosure as described and as defined in the following claims.

The invention claimed is:

1. A system comprising
a bed having at least one reader to receive wireless signals, the bed further having circuitry that controls at least one controllable function of the bed,
a first item that is coupled to a patient supported on the bed and that has a first transmitter that emits a first wireless signal that is read by the at least one reader, and
a second item that is coupled to the patient and that has a second transmitter that emits a second wireless signal that is read by the at least one reader, wherein the circuitry controls the at least one controllable function in response to the reader receiving the first wireless signal or the second wireless signal, wherein the first item comprises a wound dressing, wherein the at least one controllable function comprises adjusting inflation of a mattress of the bed in response to receipt of the first wireless signal by the at least one reader from the wound dressing.

2. The system of claim 1, wherein adjusting inflation of the mattress comprises deflating a first bladder of the mattress that is located beneath the wound dressing.

3. The system of claim 2, wherein adjusting inflation of the mattress further comprises deflating a second bladder of the mattress that is adjacent to the first bladder.

4. The system of claim 1, wherein the bed comprises a display screen coupled to the circuitry, the display screen displaying an image showing a location of the wound dressing relative to the patient on the mattress.

5. The system of claim 1, wherein the second item comprises a patient identification (ID) tag.

6. The system of claim 5, wherein the patient ID tag is included as part of a wrist band.

7. The system of claim 1, wherein the second item comprises a garment worn by a patient.

8. The system of claim 7, wherein the garment comprises at least one sock that is worn by a patient.

9. The system of claim 8, wherein the sock is color coded to indicate that the patient is a falls risk.

10. A system comprising
a bed having at least one reader to receive wireless signals, the bed further having circuitry that controls at least one controllable function of the bed,
a first item that is coupled to a patient supported on the bed and that has a first transmitter that emits a first wireless signal that is read by the at least one reader, and
a second item that is coupled to the patient and that has a second transmitter that emits a second wireless signal that is read by the at least one reader, wherein the circuitry controls the at least one controllable function in response to the reader receiving the first wireless signal or the second wireless signal, wherein the first item comprises a garment worn by a patient, wherein the bed includes a patient position monitoring system, and wherein the at least one controllable function of the bed comprises changing the patient position monitoring system from a disabled state to an enabled state in response to receipt of the first wireless signal by the at least one reader.

11. The system of claim 10, wherein the garment comprises at least one sock that is worn by a patient.

12. The system of claim 11, wherein the sock is color coded to indicate that the patient is a falls risk.

13. The system of claim 10, wherein the bed includes a brake sensor to sense whether at least one caster of the bed is braked, wherein the circuitry is configured to implement a fall prevention protocol in response to receipt of the first wireless signal by the at least one reader, and wherein the fall prevention protocol includes initiating an alert if the brake sensor indicates that the at least one caster is not braked.

14. The system of claim 10, wherein the bed includes at least one siderail position sensor to sense whether at least one siderail of the bed is in a raised position, wherein the circuitry is configured to implement a fall prevention protocol in response to receipt of the first wireless signal by the at least one reader, and wherein the fall prevention protocol includes initiating an alert if the at least one siderail position sensor indicates that the at least one siderail is not in the raised position.

15. The system of claim 10, wherein the bed includes at least one frame position sensor to sense whether an upper frame of the bed is in a lowered position, wherein the circuitry is configured to implement a fall prevention protocol in response to receipt of the first wireless signal by the at least one reader, and wherein the fall prevention protocol includes initiating an alert if the at least one frame position sensor indicates that the upper frame is not in the lowered position.

16. The system of claim 10, wherein the second item comprises a wound dressing.

17. The system of claim 10, wherein the second item comprises a patient identification (ID) tag.

18. A system comprising a bed having at least one reader to receive wireless signals, the bed further having circuitry that controls at least one controllable function of the bed, a first item that is coupled to a patient supported on the bed and that has a first transmitter that emits a first wireless signal that is read by the at least one reader, and a second item that is coupled to the patient and that has a second transmitter that emits a second wireless signal that is read by the at least one reader, wherein the circuitry controls the at least one controllable function in response to the reader receiving the first wireless signal or the second wireless signal, wherein the first item comprises a patient identification (ID) tag, and a computer that is remote from the bed, the at least on controllable function of the bed comprises transmitting to the computer patient ID data that is determined from the first wireless signal, the bed transmitting weight data corresponding to a weight of the patient as read by a weigh scale system of the bed, and the computer initiating a first alert if the weight data indicates that the patient weighs more than a weight rating of the bed.

* * * * *